(12) United States Patent
Chen et al.

US012280136B2

(10) Patent No.: US 12,280,136 B2
(45) Date of Patent: Apr. 22, 2025

(54) COMPOSITIONS CONTAINING EXOSOMES FROM ANIMAL PLACENTA, METHODS FOR PRODUCING THE SAME AND USES THEREOF

(71) Applicants: GUANGZHOU SALIAI BIOLOGICAL GENETIC ENGINEERING CO., LTD., Guangdong (CN); GUANGZHOU SALIAI STEM CELL SCIENCE AND TECHNOLOGY CO., LTD., Guangdong (CN)

(72) Inventors: Haijia Chen, Guangdong (CN); Jiaohua Jiang, Guangdong (CN); Xuejia Li, Guangdong (CN); Jiwang Xu, Guangdong (CN); Keliang Pang, Guangdong (CN); Donghuang Chen, Guangdong (CN); Aimei Zhou, Guangdong (CN); Li Tao, Guangdong (CN); Zihao Cui, Guangdong (CN); Baoyao Li, Guangdong (CN); Xinming Yan, Guangdong (CN)

(73) Assignees: GUANGZHOU SALIAI BIOLOGICAL GENETIC ENGINEERING CO., LTD., Guangdong (CN); GUANGZHOU SALIAI STEM CELL SCIENCE AND TECHNOLOGY CO., LTD., Guangdong (CN)

(*) Notice: Subject to any disclaimer, the term of this patent is extended or adjusted under 35 U.S.C. 154(b) by 461 days.

(21) Appl. No.: 17/694,715

(22) Filed: Mar. 15, 2022

(65) Prior Publication Data
US 2022/0287952 A1   Sep. 15, 2022

(30) Foreign Application Priority Data

Mar. 15, 2021 (CN) .......................... 202110275136.3
Mar. 15, 2021 (CN) .......................... 202110275137.8
Mar. 26, 2021 (CN) .......................... 202110325589.2

(51) Int. Cl.
*A61K 8/92* (2006.01)
*A61K 8/55* (2006.01)
*A61K 8/67* (2006.01)
*A61K 8/73* (2006.01)
*A61K 8/86* (2006.01)
*A61Q 19/08* (2006.01)

(52) U.S. Cl.
CPC .............. *A61K 8/925* (2013.01); *A61K 8/553* (2013.01); *A61K 8/678* (2013.01); *A61K 8/738* (2013.01); *A61K 8/86* (2013.01); *A61Q 19/08* (2013.01); *A61K 2800/622* (2013.01); *A61K 2800/624* (2013.01); *A61K 2800/65* (2013.01); *A61K 2800/84* (2013.01)

(58) Field of Classification Search
None
See application file for complete search history.

(56) References Cited

U.S. PATENT DOCUMENTS

2021/0046172 A1* 2/2021 Gho .......................... C12N 1/20

FOREIGN PATENT DOCUMENTS

| CN | 101703259 A | 5/2010 |
|---|---|---|
| CN | 103265612 A | 8/2013 |
| CN | 104488850 A | 4/2015 |
| CN | 108143750 A | 6/2018 |
| CN | 110051554 A | 7/2019 |
| CN | 110151679 A | 8/2019 |
| CN | 110548001 A | 12/2019 |
| CN | 110772538 A | 2/2020 |
| CN | 110859798 A | 3/2020 |
| CN | 110897993 A | 3/2020 |
| CN | 111450061 A | 7/2020 |
| WO | 2018/140363 A1 | 8/2018 |

OTHER PUBLICATIONS

Tansey, H. "Centrifugation: Best Practices for Reliable, Reproducible Results", LabCompare.com, Feb. 14, 2018. https://www.labcompare.com/10-featured-articles/347135-centrifugation-best-practices-for-reliable-reproducible-results/ (Year: 2018) (Year: 2018).*
OpsDiagnostics "Sonication 101", http://web.archive.org/web/20090105175222/http://www.opsdiagnostics.com/notes/ranpri/rpsonication101.htm (Year: 2009) (Year: 2009).*
Zhou, H, et al. Collection, storage, preservation, and normalization of human urinary exosomes for biomarker discovery. Renal Diagnostics and Therapeutics Unit, NIDDK, Bethesda, MD, USA. Kidney International (2006) 69, 1471-1476. http://www.kidney-international.org (Year: 2006) (Year: 2006).*
Sidhom, K. et al. A Review of Exosomal Isolation Methods: Is Size Exclusion Chromatography the Best Option? International Journal of Molecular Sciences 2020, 21, 6466. Sep. 4, 2020. (Year: 2020) (Year: 2020).*
First Office Action dated Jul. 27, 2022 for Chinese patent application No. 202110275137.8, English translation provided by Global Dossier.
Jiao Yanli et al., "Study on Ultrasonic Extraction of Activity Protein from Sheep Placenta", Food and fermentation Industry, Nov. 30, 2011, pp. 224-228.

(Continued)

*Primary Examiner* — Robert M Kelly
*Assistant Examiner* — John David Moore
(74) *Attorney, Agent, or Firm* — Yue (Robert) Xu; Apex Attorneys at Law, LLP (57) ABSTRACT

Disclosed are a method for preparing exosomes from bovine placenta, lyophilized powder of the exosomes, as well as a composition containing exosomes from animal placenta and a preparation method and use thereof in anti-wrinkle on skin.

1 Claim, 6 Drawing Sheets

(56) References Cited

OTHER PUBLICATIONS

First Office Action dated Sep. 22, 2021 for Chinese patent application No. 202110325589.2, English translation provided by Global Dossier.

Guangzhou Celera Bio-Gene Engineering Co., Ltd., "CPE umbilical cord exosome anti-aging freeze-dried powder + umbilical cord exosome anti-aging essence", Feb. 25, 2021.

Feng Qing et al., "Nutrition and Beauty—Uncovering the Mysteries of Health and Beauty", Huazhong University of Science and Technology Press, Mar. 31, 2013, 2nd last paragraph on p. 166.

Cong Fengsong, "Biochemical experiments", Shanghai Jiaotong University Press, Jan. 31, 2013, 2nd last paragraph on p. 73-7th paragraph on p. 74.

* cited by examiner

COMPOSITIONS CONTAINING EXOSOMES FROM ANIMAL PLACENTA, METHODS FOR PRODUCING THE SAME AND USES THEREOF

CROSS REFERENCE TO RELATED APPLICATIONS

This application claims the priority of Chinese Patent Application No. 202110275137.8 filed on Mar. 15, 2021, Chinese Patent Application No. 202110275136.3 filed on Mar. 15, 2021 and Chinese Patent Application No. 202110325589.2 filed on Mar. 26, 2021, which are hereby incorporated by reference in their entirety.

FIELD

The present disclosure relates to the field of biotechnology, and specifically relates to a method for preparing exosomes from bovine placenta, lyophilized powder of the exosomes, as well as a composition containing exosomes from animal placenta and a preparation method and use thereof.

BACKGROUND

In recent years, with the increase of research on animal placenta, the physiological activities of many animal placentas, such as placentas from cattle, sheep, deer and donkeys, have been continuously discovered. Animal placenta extract is a kind of compound active ingredients derived from animal placenta, rich in amino acids, proteins, lecithin, polysaccharides, vitamins, mineral elements, etc., and has the functions of enhancing memory, anti-stress, regulating endocrine, enhancing immunity, anti-aging and the like. According to the current relevant research, placenta extract has various biological effects such as promoting peripheral blood circulation, facilitating cell and tissue respiration, removing free radicals, moisturizing, immune activation and beauty.

At present, the methods for obtaining placenta extract are mainly the following three: (1) Direct extraction: homogenizing the placental tissue and then adding an extracting solution to extract; or homogenizing the placenta and then performing multiple freeze-thaws, extraction, centrifugation of the extract and lyophilization. (2) Supercritical $CO_2$ extraction: after freeze-drying, crushing and supercritical extraction of placental tissue, then homogenizing the extract, performing centrifugation and lyophilization of the centrifugate. (3) Enzyme-assisted extraction: moderately hydrolyzing the placenta by one or two proteases, performing centrifugation and lyophilization. The preparation methods of these placenta extracts and products have the following disadvantages: (1) the obtained placenta extracts are mainly macromolecular proteins, and the absorption efficiency of the human body is low; (2) there is a lack of refining process for extract, and the product has complex components and low quality; and (3) the methods of extraction are simple and extensive, and both of the extraction efficiency and the utilization rate of raw materials are low. Therefore, a method that can efficiently obtain the biologically active ingredients in the animal placenta and fully retain their efficacy is urgently needed.

Exosomes are membranous vesicles secreted by the intracellular vesicle structure to the outside of the cell, with a diameter of about 30-150 nm. Cells secrete exosomes under normal physiological conditions, and exosome-like vesicles are secreted into the extracellular space through exocytosis. Exosomes selectively encapsulate a variety of biologically active substances such as lipids, proteins, mRNAs and miRNAs, which can be transdermally absorbed and taken up by target cells, and can reduce the degree of tissue damage and promote the morphological and functional repair of damaged tissue. Exosomes also have potential biological functions such as regulating immunity, cell growth and differentiation. Bovine placentas have abundant sources, containing a large number of high-quality proteins and plenty of active enzymes, with the similar composition of human placenta. Therefore, the establishment of a method for extracting exosomes from animal placenta can lay the foundation for the research and development and industrialization of new raw materials of cosmetic based on animal exosomes.

However, the current preparation process is mainly based on the preparation of placenta extract, not for exosomes, and the preparation process is simple and extensive, the extraction efficiency is low, and the product composition is complex. Besides, there is a lack of uniform quality control standards, which ultimately leads to the inability to form safe, stable and reliable products.

Lyophilized powder is a powdery solid obtained by removing moisture from the raw material by vacuum lyophilization. The vacuum lyophilization method is widely used in pharmaceutical production. The main process is to completely freeze the raw materials at a low temperature, so that the active material and the protective agent form a stable solid skeleton, then directly sublime the solid ice crystals under high vacuum and low temperature conditions, and use the method of condensation to capture the sublimated water vapor, causing the material dehydrate and dry. Lyophilized powder has loose and porous texture, accurate quantification and no pollution, which can avoid the decomposition and deterioration of active substances due to high heat; after adding water for injection, the original characteristics can be quickly restored; in addition, the active substances are not easily oxidized in a high vacuum environment, which is conducive to long-term storage of products and is a common dosage form of pharmaceutical preparations.

In the cosmetic industry, many biologically active substances (for example, some plant-derived or bioengineered-derived substances) have poor stability in cosmetic systems and are easily degraded and deteriorated. The widespread development and popularization of vacuum lyophilization technology has solved this problem, and cosmetics in lyophilized powder have also emerged as the times require. Because of the high stability and convenience of transportation, storage and use, lyophilized powder has now become a common form of cosmetic ingredients with the popularization of vacuum lyophilization technology and the reduction of costs.

The key to the application of exosomes lies in the large-scale production of safe and qualified exosomes and their stable storage. The current lyophilization method designed for exosomes can preserve the activity of exosomes to a certain extent, but the reagents are complex in components and cumbersome for preparation, and the activity of exosomes is not stable, which is not conducive to the quality control of exosome products. Therefore, there is an urgent need for a cryopreservation reagent with simple components, which can preserve exosomes for a long time at room temperature without affecting their activity, and a preparation method thereof.

The skin is the largest organ on the surface of the human body. It is in direct contact with the external environment and resists external oxidation, drying, ultraviolet rays and other factors. In addition, due to the influence of internal factors such as age, diet, living habits and work pressure, the free radicals in the skin cells increase and the collagen is lost, causing the skin to lose water and nutrients, thereby leading to skin aging and wrinkles. For a long time, in the face of skin aging and wrinkles, people have used various means to cover up and treat them.

Relevant studies in modern biology and medicine have demonstrated that cellular exosomes can be used externally on the human body, can be absorbed transdermally, and can introduce functional proteins, natural moisturizing factors and other substances into cells, which can supplement the skin with sufficient moisture, collagen, fibrin and cytokines stimulating protein production, promote the formation of collagen fibers, reticular fibers and elastic fibers, and play an efficient and safe role in promoting skin repair and delaying skin aging.

Exosomes exist in the form of vesicles. During the production, storage and transportation of products containing cellular exosomes on the market, because the cellular exosomes directly contact other components in the product, such as emulsifiers, ions, etc., the vesicles of the cellular exosomes are easily ruptured, resulting in the outflow of their internal active ingredients, oxidization or denaturation, which reduces the efficacy of skin care products. When using skin care products, the vesicle structure of exosomes is easily broken during the applying process, and most exosomes release internal active ingredients in a short period of time, so that the active ingredients are quickly oxidized or denatured, resulting in less lasting skin care effects. In addition, the products containing cellular exosomes on the market have low transparency and cannot be added in large quantities in transparent products, which limits their use.

SUMMARY

In a first aspect, the present disclosure provides a method for preparing exosomes derived from bovine placenta. The method has high extraction rate of exosomes from bovine placenta, good process stability, and the obtained exosomes from bovine placenta have good integrity and biological activity.

In some embodiments, the method for preparing exosomes derived from bovine placenta comprises:
homogenizing bovine placenta to obtain a homogenate, and subjecting the homogenate to freeze-thaw;
performing a first round of ultrasonic treatment on the thawed homogenate and filtering, and freezing the filtrate at −80° C.; and
thawing the filtrate at 4° C. and centrifuging to obtain a supernatant, performing a second round of ultrasonic treatment on the supernatant, and performing multiple filtration through filters to obtain the exosomes from bovine placenta;
wherein the second round of ultrasonic treatment is performed once at an interval of 8 s, each ultrasonic treatment is lasted for 8 s, the power of the second round of ultrasonic treatment is 100-700 w, and the total time of ultrasonic treatment is 30-60 min.

In the present disclosure, the freeze-thaw comprises freezing at −80° C. for 12-24 h and then thawing at room temperature. The number of freeze-thaw is 1-5 times. In some specific embodiments, it is specifically 3 times.

In some embodiments, the power of the first round of ultrasonic treatment is 990 w and the time is 30 min.

In some embodiments, the homogenate after the first round of ultrasonic treatment is filtered through 20-mesh and 80-mesh filters in sequence.

In some specific embodiments, the second round of ultrasonic treatment is performed once at an interval of 8 s, each ultrasonic treatment is lasted for 8 s, the total time of ultrasonic treatment is 30 min or 60 min, and the power of ultrasonic treatment is 500 w or 700 w.

In the present disclosure, the multiple filtration is four times of filtration. In some embodiments, the four times of filtration is to filter through filter with pore sizes of 5 μm, 1 μm, 0.45 μm and 0.22 μm in sequence.

In the present disclosure, the centrifugation is differential centrifugation. In some embodiments, the differential centrifugation comprises: centrifuging at 300 g for 30 min, taking supernatant for centrifuging at 3,000 g for 30 min, and taking supernatant again for centrifuging at 10,000 g for 30 min.

In some embodiments, the method further comprises pre-treating the bovine placenta before homogenizing; wherein, the pre-treating specifically comprises: removing the amniotic membrane and the umbilical cord from the placenta, washing the placenta repeatedly until the blood is removed and drained.

The method for preparing exosomes from bovine placenta of the present disclosure comprises: homogenizing bovine placenta to obtain a homogenate, and subjecting the homogenate to freeze-thaw; performing a first round of ultrasonic treatment on the thawed homogenate and filtering, and freezing the filtrate at −80° C.; and thawing the filtrate at 4° C. and centrifuging to obtain a supernatant, performing a second round of ultrasonic treatment on the supernatant, and performing multiple filtration through filters to obtain the exosomes from bovine placenta; wherein the second round of ultrasonic treatment is performed once at an interval of 8 s, each ultrasonic treatment is lasted for 8 s, the power of the second round of ultrasonic treatment is 100-700 w, and the total time of ultrasonic treatment is 30-60 min. Compared with the prior art, the method for preparing exosomes from bovine placenta of the present disclosure has the following beneficial effects:

1) The method of the present disclosure completely adopts the method of physical extraction and maintains the low temperature environment during the entire extraction process, avoiding the unfavorable factors such as enzymes, organic solvents or high temperature introduced by other preparation processes that affect product quality and activity.

2) The method of the present disclosure is different from the conventional extraction process for placenta, but combines the structural characteristics of the placenta to gradually remove other components through physical methods such as freeze-thaw, ultrasonic treatment and filtration, and finally obtains sterile exosome-rich product. Through a series of identification experiments and functional verification experiments, it is confirmed that the bovine placenta prepared by the present disclosure has good integrity and biological activity, and has a significant effect of promoting the proliferation of human skin fibroblasts. The method for preparing exosomes from bovine placenta established by the present disclosure has good reliability and stability.

In a second aspect, the present disclosure provides a lyophilized powder of exosomes from bovine placenta and a preparation method thereof. The lyophilized powder has good stability and biological activity, and can be stored for a long time at room temperature.

The method for preparing lyophilized powder of exosomes from bovine placenta of the present disclosure comprises:
mixing the exosomes from bovine placenta with an excipient to obtain a mixture, and
pre-freezing, freezing, vacuumizing, and vacuum drying the mixture;
wherein the excipient is composed of mannitol, trehalose, glycine, glycerol, Tween, albumin and water.

In some embodiments, the volume ratio of the exosomes from bovine placenta to the excipient is 1:1.

In some embodiments, the excipient is composed of the following components by mass percentage:
2.0%-10.0% mannitol, 0.1%-1.0% trehalose, 0.05%-1.0% glycine, 1.0%-5.0% glycerol, 0.01%-0.05% Tween, 0.1%-0.5% albumin, and the balance is water.

In some specific embodiments, the excipient is composed of the following components by mass percentage:
3.0% mannitol, 0.4% trehalose, 0.3% glycine, 2.0% glycerol, 0.02% Tween, 0.2% albumin, and the balance is water.

In some specific embodiments, the excipient is composed of the following components by mass percentage:
10.0% mannitol, 0.1% trehalose, 0.05% glycine, 5.0% glycerol, 0.01% Tween, 0.1% albumin, and the balance is water.

In some specific embodiments, the excipient is composed of the following components by mass percentage:
5.0% mannitol, 0.4% trehalose, 0.06% glycine, 4.0% glycerol, 0.02% Tween, 0.2% albumin, and the balance is water.

In some embodiments, the pre-freezing comprises cooling the mixture to −40° C. and maintaining for 190 min.

In some embodiments, the freezing comprises freezing the pre-frozen mixture by cooling from −40° C. to −50° C. in 1 min.

In some embodiments, the vacuum drying comprises a first vacuum drying and a second vacuum drying.

Further, the first vacuum drying comprises: heating from −50° C. to −15° C. in 70 min and maintaining for 5 h; heating from −15° C. to −10° C. in 60 min and maintaining for 5 h; heating from −10° C. to −5° C. in 60 min and maintaining for 5 h; and heating from −5° C. to 0° C. in 60 min and maintaining for 220 min.

The second vacuum drying comprises: heating from 0° C. to 30° C. in 40 min and maintaining for 500 min at a vacuum degree of 0.19 bar; and maintaining at 30° C. for 120 min at a vacuum degree of 0.0002 bar.

After the second vacuum drying, residual moisture is removed as much as possible.

In the present disclosure, the above pre-freezing, the first vacuum drying and the second vacuum drying are all performed in a lyophilizer. After the second vacuum drying is completed, starting the hydraulic system of the lyophilizer to press the plug. After the plug is pressed, check whether the plug jumps out. If there is no abnormality, release the vacuum in the lyophilizer.

In some embodiments, the exosomes from bovine placenta are prepared according to the method in the first aspect.

The present disclosure also provides the lyophilized powder of exosomes from bovine placenta prepared by the above preparation method.

In a specific embodiment, the present disclosure tested the function of lyophilized powder of exosomes from bovine placenta, and the morphological identification results showed that the exosomes reconstituted from the lyophilized powder of exosomes from bovine placenta was uniform in size and had a round-cake structure with low refraction in the middle and high refraction around. The expression of CD63 and TSG101 proteins was detected by western blotting, and it was found by CCK8 detection that the exosomes significantly promoted cell proliferation. The above results show that the method for preparing lyophilized powder of exosomes from bovine placenta of the present disclosure is suitable for the freezing storage of exosomes from bovine placenta, and the prepared lyophilized powder of exosomes from bovine placenta can maintain good stability and biological activity.

The present disclosure also provides use of the lyophilized powder of exosomes from bovine placenta in the manufacture of anti-aging or repair cosmetics.

In the present disclosure, the excipient comprises mannitol, trehalose, glycine, glycerol, Tween, albumin and water are combined with the preparation method of the present disclosure, and the prepared lyophilized powder of exosomes from bovine placenta has good stability and biological activity, which can be stored at room temperature for a long time, and has obvious advantages over the existing lyophilization method. Experiments show that exosomes from bovine placenta still maintain good integrity and biological activity after being stored at room temperature of 25° C. for 6 months and thus is suitable for long-term preservation and application of exosomes from bovine placenta.

In a third aspect, the present disclosure provides a composition containing exosomes from animal placenta and a preparation method and use thereof.

The composition containing exosomes from animal placenta of the present disclosure, by mass percentage, comprises:

| | |
|---|---|
| lyophilized powder of exosomes from animal placenta | 0.05-5%; |
| humectant | 1-20%; |
| material for microencapsulation | 0.05-5%; |
| vitamin E derivative | 0.01-2%; |
| water | the balance; | wherein, the material for microencapsulation is selected from the group consisting of soybean lecithin, hydrogenated soybean phospholipid, hydroxylated lecithin, cyclodextrin, hydroxypropyl cyclodextrin and a combination thereof.

In another embodiment, the material for microencapsulation is selected from hydroxylated lecithin or/and hydroxypropyl cyclodextrin.

In another embodiment, the material for microencapsulation is hydroxylated lecithin.

In another embodiment, the lyophilized powder of exosomes from animal placenta is selected from the group consisting of lyophilized powder of exosomes from horse placenta, lyophilized powder of exosomes from porcine placenta, lyophilized powder of exosomes from ovine placenta, lyophilized powder of exosomes from bovine placenta, lyophilized powder of exosomes from deer placenta and a combination thereof.

In another embodiment, the lyophilized powder of exosomes from animal placenta is selected from lyophilized powder of exosomes from bovine placenta or/and lyophilized powder of exosomes from ovine placenta.

In another embodiment, the lyophilized powder of exosomes from animal placenta is lyophilized powder of exosomes from bovine placenta.

Specifically, the lyophilized powder of exosomes from animal placenta is prepared by lyophilization of the exosomes derived from animal placenta.

In another embodiment, the humectant is selected from the group consisting of polyol, plant polysaccharide, sodium hyaluronate, sodium PCA, ceramide and a combination thereof.

In another embodiment, the humectant is selected from polyol or/and sodium hyaluronate.

Specifically, the polyol is selected from the group consisting of glycerol, butanediol, 1,2-butanediol, propanediol, 1,3-propanediol, 1,2-pentanediol, 1,2-hexanediol, dipropylene glycol, polyethylene glycol-8, polyethylene glycol-10, polyethylene glycol-14, polyethylene glycol-32, sorbitol, glucose and a combination thereof.

In another embodiment, the humectant is selected from glycerol or butanediol.

In another embodiment, the humectant is polyol and sodium hyaluronate, and the mass ratio of the polyol to sodium hyaluronate is (10-20):1.

In another embodiment, the vitamin E derivative is selected from the group consisting of tocopherol acetate, tocopherol phosphate, tocopherol glucoside, tocopherol polyether and a combination thereof.

In another embodiment, the vitamin E derivative is selected from tocopherol acetate or/and tocopherol glucoside.

In another embodiment, the vitamin E derivative is Tocopherol acetate.

In another embodiment, the composition further comprises amino acid;

In another embodiment, by mass percentage, the composition comprises:

| | |
|---|---|
| lyophilized powder of exosomes from animal placenta | 0.05-5%; |
| humectant | 1-20%; |
| material for microencapsulation | 0.05-5%; |
| amino acid | 0.1-5%; |
| vitamin E derivative | 0.01-2%; |
| water | the balance. |

In another embodiment, the amino acid is selected from the group consisting of glycine, tryptophan, threonine, arginine, glutamic acid, polyglutamic acid, proline, lysine, citrulline, valine, methionine, leucine, serine and a combination thereof.

In another embodiment, the transmittance of the composition is not lower than 60% of the transmittance of pure water under the same test conditions.

In another embodiment, the composition further comprises amino acid; by mass percentage, the composition comprises:

| | |
|---|---|
| lyophilized powder of exosomes from animal placenta | 0.05-2%; |
| humectant | 2-15%; |
| material for microencapsulation | 0.1-3%; |
| amino acid | 0.5-3%; |
| vitamin E derivative | 0.05-1.5%; |
| water | the balance. |

In another embodiment, the transmittance of the composition is not lower than 70% of the transmittance of pure water under the same test conditions.

In another embodiment, the composition further comprises amino acid; by mass percentage, the composition comprises:

| | |
|---|---|
| lyophilized powder of exosomes from animal placenta | 0.1-1%; |
| humectant | 5-10%; |
| material for microencapsulation | 0.5-2%; |
| amino acid | 1-2%; |
| vitamin E derivative | 0.1-1%; |
| water | the balance. |

In another embodiment, the transmittance of the composition is not lower than 80% of the transmittance of pure water under the same test conditions.

The present disclosure also provides a method for preparing the composition, comprising:
  heating, dissolving and mixing the humectant, the material for microencapsulation and water, and cooling to 20-50° C. to prepare a first mixture;
  mixing the lyophilized powder of exosomes from animal placenta and the vitamin E derivative to prepare a second mixture; and;
  mixing the second mixture and the first mixture to obtain the composition containing exosomes from animal placenta.

In another embodiment, the method for preparing the composition comprises:
  mixing the humectant, the material for microencapsulation and water, heating and stirring at 60° C.-80° C., and after the solid is completely dissolved, cooling down to 20-50° C. to prepare a first mixture; and
  mixing the lyophilized powder of exosomes from animal placenta, the amino acid and the vitamin E derivative uniformly to prepare a second mixture; and adding the second mixture to the cooled first mixture and stirring well to obtain the composition containing exosomes from animal placenta.

The present disclosure also provides use of the above-mentioned composition containing exosomes from animal placenta in the manufacture of products for anti-wrinkle on skin.

Specifically, the above-mentioned composition containing exosomes from animal placenta of the present disclosure is used to prepare anti-wrinkle and repair cosmetics.

Specifically, the cosmetic is selected from the group consisting of toner, essence, primary liquid, facial mask, body lotion, lotion, face cream and eye cream.

In another embodiment, the cosmetic is essence.

In another embodiment, the essence comprises water, cosmetic additive, and the composition containing exosomes.

Specifically, the cosmetic additive is selected from the group consisting of humectant, chelating agent, thickening agent, preservative, moisturizing agent, anti-sensitizer, fragrance suitable for cosmetics, plant extract suitable for cosmetics and a combination thereof.

Specifically, the cosmetic additive is selected from the group consisting of glycerol, butanediol, disodium EDTA, ammonium acryloyldimethyltaurate/VP copolymer, methylparaben, phenoxyethanol, allantoin, leaf extract of Aloe Barbadensis, ethylhexylglycerol and a combination thereof.

The present disclosure provides a composition containing exosomes from animal placenta, comprising lyophilized powder of exosomes from animal placenta, a humectant, a material for microencapsulation, a vitamin E derivative and water, wherein the material for microencapsulation is located on the outer surface of the exosomes from animal placenta to form a microcapsule structure to avoid the destruction of the vesicle structure of the exosomes; in addition, amino acids can improve the encapsulation efficiency of exosomes from animal placenta by the material for microencapsulation. Therefore, the storage and transportation of the exosomes from animal placenta is simpler and more convenient, and the storage and transportation cost is also reduced. From the experimental data provided by the present disclosure, it can be seen that the composition containing exosomes of the present disclosure exists in a complete microcapsule structure under the transmission electron microscope, and the material for microencapsulation has a good protective effect on exosomes from animal placenta. It can be seen that in the process of storage and transportation of the composition containing exosomes of the present disclosure, the material for microencapsulation will be attached to the outer surface of the exosomes from animal placenta to form a microcapsule structure to avoid the destruction of the vesicle structure of the exosomes; in addition, amino acids can improve the encapsulation efficiency of exosomes from animal placenta by the material for microencapsulation. The composition containing exosomes of the present disclosure has excellent light transmittance with the transmittance not lower than 60% of the transmittance of pure water under the same test conditions, and can be directly used in skin care products of a transparent system without producing a turbid state. Furthermore, the composition containing exosomes of the present disclosure has a wide range of raw material sources and a simple preparation method, and is suitable for large-scale production.

In addition, the composition containing exosomes provided by the present disclosure can be prepared into different forms of cosmetics or skin care products. For products comprising the composition containing exosome of the present disclosure, on the one hand, the microcapsule structure protects the vesicle structure of the exosomes from animal placenta in the skin care product from destruction, and the exosomes remain active for a long time during the storage and transportation of skin care products; on the other hand, the microcapsules are not immediately broken when the skin care products are applied, and during the residence of skin care products on the skin, the microcapsule structure gradually disintegrates, and the active substances in the exosomes from animal placenta are slowly released to the skin, which can achieve a lasting skin care effect.

DETAILED DESCRIPTION

Those skilled in the art can implement the present disclosure by learning from the content herein and appropriately improving the process parameters. It should be particularly noted that all similar substitutions and modifications are obvious to those skilled in the art, and they are all considered to be included in the present disclosure. The method and use of the present disclosure have been described through the preferred embodiments, and it is apparent that relevant persons can make changes or appropriate modifications and combinations of the methods and use herein without departing from the content, spirit and scope of the present disclosure to implement and apply the present disclosure.

The materials used in the present disclosure are all commercially available. The sodium PCA is sodium pyrrolidone carboxylate; the UV spectrophotometer involved is Japan Shimadzu UV-2700, the transmission electron microscope is Japan JEM-3200FS, and the skin tester is American Visia.

Bovine placenta, purchased from dairy farms, was bovine placenta naturally delivered by healthy cows. After being qualified by testing virus and bacteria, the bovine placenta was washed repeatedly with water, cut into pieces, packaged and stored frozen at −80° C. The lyophilized powder of exosomes from horse placenta, lyophilized powder of exosomes from porcine placenta, lyophilized powder of exosomes from ovine placenta and lyophilized powder of exosomes from deer placenta were commercially available general products.

The present disclosure is further illustrated below in conjunction with examples.

Example 1 Preparation of Exosomes from Bovine Placenta 1) 500 g of bovine placenta tissue frozen at −80° C. was weighed and thawed at room temperature.

2) After the tissue was completely thawed, it was minced with an automatic meat grinder.

3) The tissue was homogenized using a tissue homogenizer to prepare a uniform homogenate.

4) The homogenate was frozen at −80° C. for 24 h and then thawed at room temperature. Such freeze-thaw was repeated 3 times to fully broken the placental cells.

5) The thawed homogenate was subjected to a first round of ultrasonic treatment (990 w, 30 min) to further break cells and release exosomes from bovine placenta.

6) The homogenate after the first round of ultrasonic treatment was filtered through stainless steel filters with different pore sizes (20 mesh and 80 mesh) to remove insoluble substances, and the filtrate was collected and frozen at −80° C.

7) Centrifugation: The filtrate of the bovine placenta extract obtained in step 6) was thawed at 4° C. and then centrifuged under different centrifugal forces (300 g, 30 min; 3000 g, 30 min; 10,000 g, 30 min) in sequence. The supernatant from the previous centrifugation was further centrifuged to fully remove insoluble substances in the filtrate.

8) The supernatant obtained in the last centrifugation (10,000 g, 30 min) of step 7) was subjected to a second round of ultrasonic treatment. The second round of ultrasonic treatment was performed once at an interval of 8 s, each ultrasonic treatment was lasted for 8 s, the power of ultrasonic treatment was 500 w and the total time of ultrasonic treatment was 30 min.

9) Filtration: The mixture after ultrasonic treatment was subjected to multiple filtration (the pore size of the filter was 5 μm, 1 μm, 0.45 μm and 0.22 μm in sequence) to obtain exosomes from bovine placenta (labeled as Exo-00).

Example 2

In step 8), the second round of ultrasonic treatment was performed once at an interval of 8 s, each ultrasonic treatment was lasted for 8 s, the power of ultrasonic treatment was 700 w and the total time of ultrasonic treatment was 30 min.

Other steps were the same as in Example 1.

Example 3

In step 8), the second round of ultrasonic treatment was performed once at an interval of 8 s, each ultrasonic treatment was lasted for 8 s, the power of ultrasonic treatment was 500 w and the total time of ultrasonic treatment was 60 min.

Other steps were the same as in Example 1.

Example 4

In step 8), the second round of ultrasonic treatment was performed once at an interval of 8 s, each ultrasonic treatment was lasted for 8 s, the power of ultrasonic treatment was 700 w and the total time of ultrasonic treatment was 60 min.

Other steps were the same as in Example 1.

Example 5

Comparative Examples 1~4 were set up, wherein the ultrasonic parameters of step 8) in the preparation method of Comparative Examples 1~4 are shown in Table 1, and other steps were the same as in Example 1.

TABLE 1

| Experiment Group | Power | Total Ultrasound Time (min) | Ultrasound Running/Stopping Time (s/s) |
|---|---|---|---|
| Group 1 (Comparative Example 1) | 100 w | 30 | 8/8 |
| Group 2 (Comparative Example 2) | 300 w | 30 | 8/8 |
| Group 3 (Example 1) | 500 w | 30 | 8/8 |
| Group 4 (Example 2) | 700 w | 30 | 8/8 |
| Group 5 (Comparative Example 3) | 100 w | 60 | 8/8 |
| Group 6 (Comparative Example 4) | 300 w | 60 | 8/8 |
| Group 7 (Example 3) | 500 w | 60 | 8/8 |
| Group 8 (Example 4) | 700 w | 60 | 8/8 |

Figure 1:
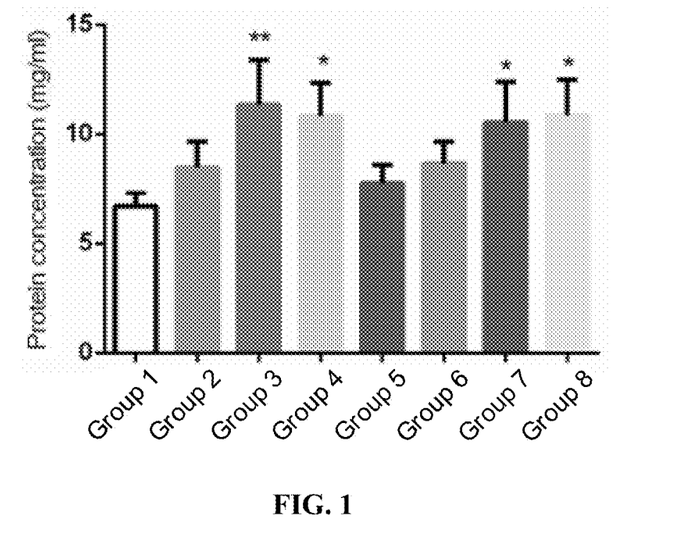
FIG. 1 shows the effect of different ultrasound parameters on the protein concentration of exosomes from bovine placenta.

Identification of Exosomes from Bovine Placenta
1) Protein Concentration Assay:

The prepared exosomes from bovine placenta were measured for protein concentration using the BCA method. The results showed that the protein concentration of Examples 1~4 was significantly higher than that of Comparative Examples 1-4, with the protein concentration of exosomes from bovine placenta prepared in Example 1 being 11.33±2.09 (mg/ml) (group 3, n=6) (as shown in FIG. 1).

2) Exosome Identification

Figure 2:
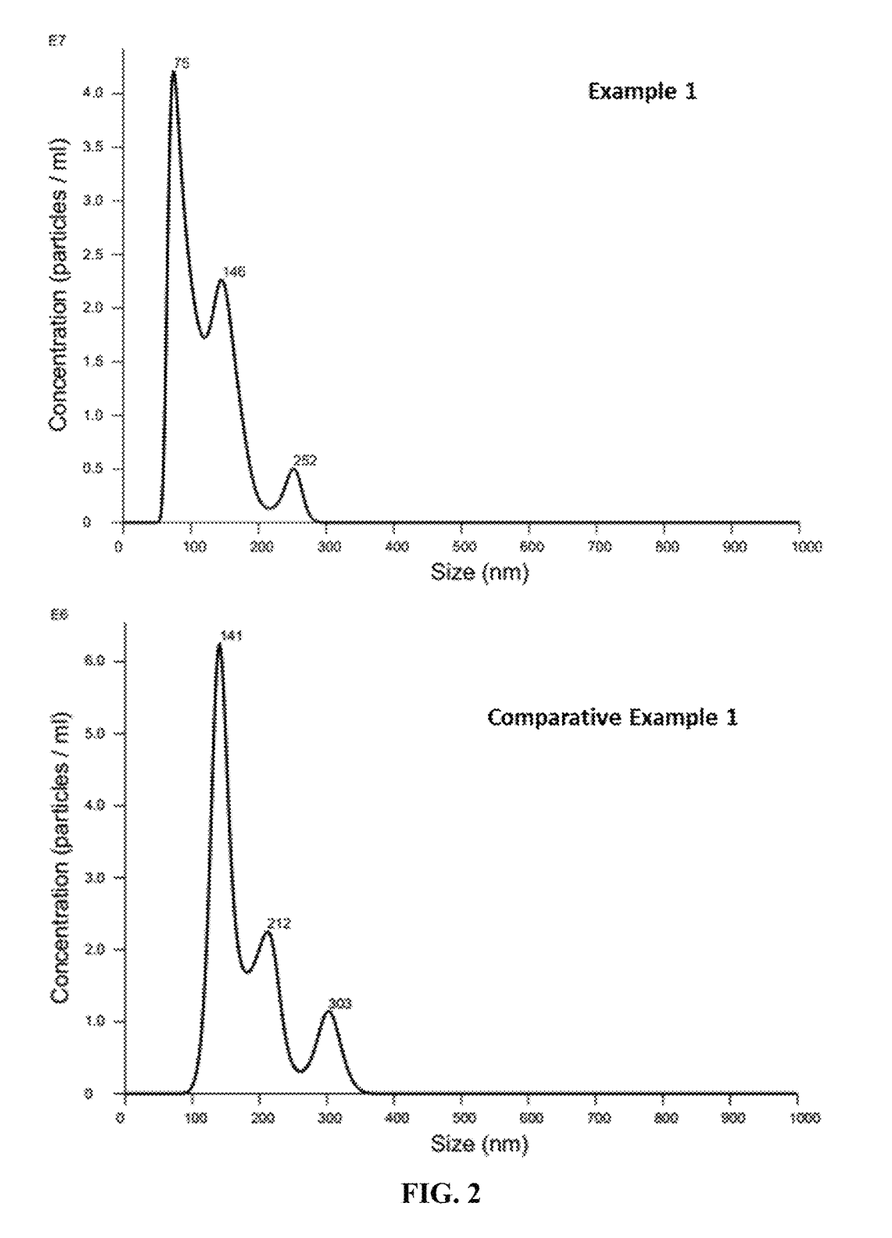
FIG. 2 shows the results of particle size analysis of exosomes from bovine placenta prepared in Example 1 and Comparative Example 1.

The products obtained in Example 1 and Comparative Example 1 were subjected to particle size analysis using Nanosight NS300. As shown in FIG. 2, the distribution of particle sizes are mainly in the range of 30-150 nm, which is consistent with the size range of exosomes. Compared with the Comparative Example 1, Example 1 contained more particles with the sizes in the range of exosomes.

Figure 3:
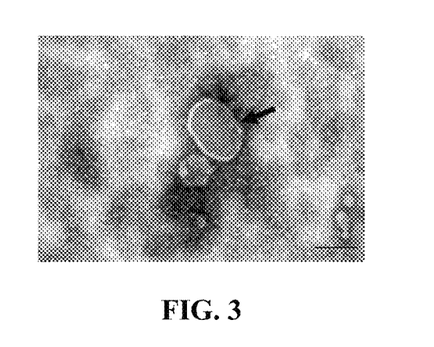
FIG. 3 shows the electron microscope picture of exosomes from bovine placenta prepared in Example 1.

The product obtained in Example 1 was observed by electron microscope. As shown in FIG. 3, there are vesicles in the obtained product, which have round pie structure with low refractive index in the middle and high around, in line with the classical structure of exosomes.

Figure 4:
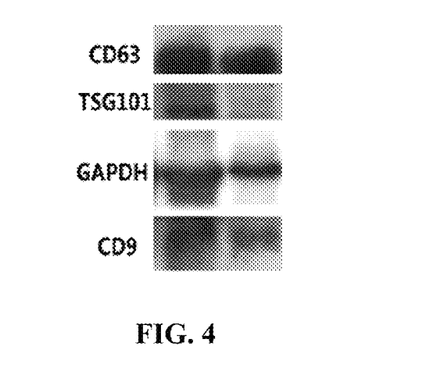
FIG. 4 shows the results of western blotting analysis of exosomes from bovine placenta prepared in Example 1.

The product obtained in Example 1 was subjected to western blotting analysis to detect the biomarkers of exosomes, CD63, TSG101 and CD9, and GAPDH was the loading control. As shown in FIG. 4, CD63, TSG101 and CD9 were detected in the product.

The above results show that the main component of the product obtained by the preparation method of the present disclosure is exosomes.

Efficacy Assessment of Exosomes from Bovine Placenta

Figure 5:
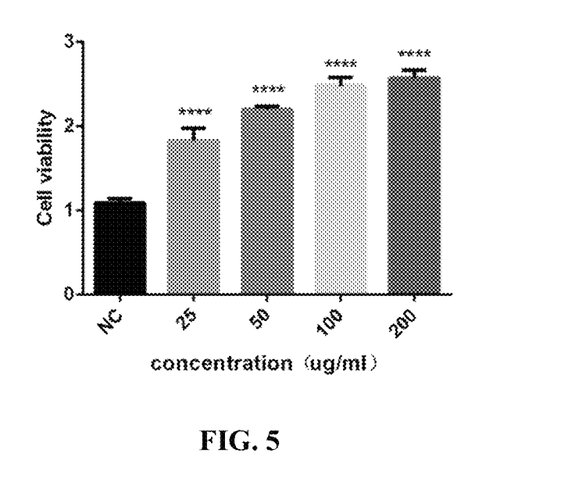
FIG. 5 shows the efficacy assessment of the exosomes from bovine placenta prepared in Example 1 on the proliferation of human skin fibroblasts.

The product obtained in Example 1 was assessed for the proliferative effect on human skin fibroblasts. CCK8 method was used to detect the activity of exosomes from bovine placental prepared in Examples 1. Human skin fibroblasts cells (HSF) were cultured for 24 hours, exosomes were added to the culture medium according to a concentration gradient (0, 25, 50, 100, 200 μg/ml), and NC was a negative control without exosomes. After culturing for 48 hours, CCK8 reagent was added to the cells and incubated for 2 hours, and then the OD450 was measured by using a microplate reader, and the cell viability was calculated. As shown in FIG. 5, the exosomes from bovine placenta prepared by the present disclosure had a significant effect of promoting the proliferation of human skin fibroblasts in the concentration range of 25-200 μg/mL.

Example 6 Preparation of Lyophilized Powder of Exosomes from Bovine Placenta

The extract of exosomes from bovine placenta obtained by the method of Example 1 was thawed at room temperature and mixed with excipients (3.0% mannitol, 0.4% trehalose, 0.3% glycine, 2.0% glycerol, 0.02% Tween, 0.2% albumin, and the balance is water) in a volume ratio of 1:1 to obtain a mixture. The mixture was subjected to lyophilization in a sterile environment using a Tofflon's lyophilizer according to the procedure in Table 2 (including pre-freezing, freezing, vacuumizing, primary sublimation and vacuum drying), and the maximum temperature during the lyophilization process should not exceed 40° C. The lyophilized powder of exosomes from bovine placenta was prepared, labeled as Exo-01.

Figure 6:
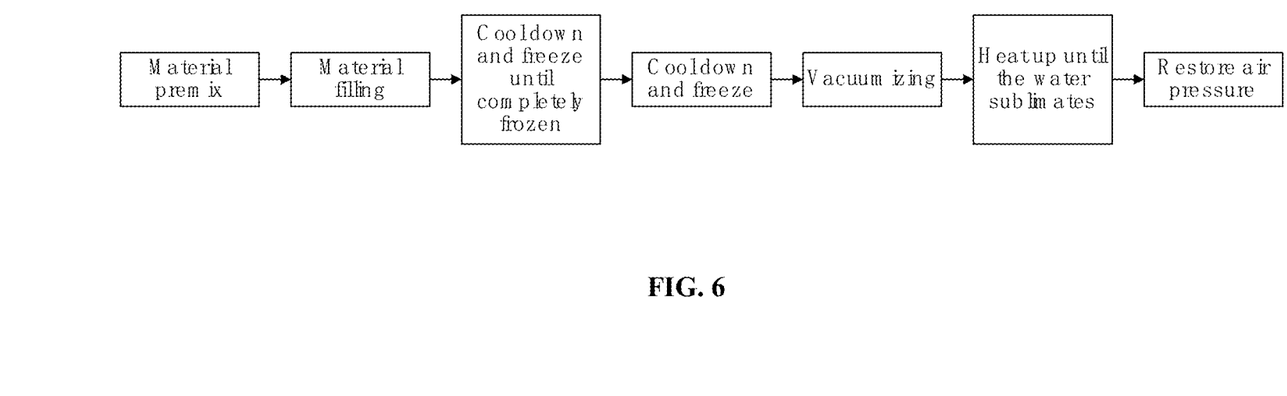
FIG. 6 shows the preparation process flow chart of the lyophilized powder of exosomes of the present disclosure.

Preparation process is with reference to FIG. 6 and parameter setting to Table 2. The specific steps are as follows:

(1) Filling: The prepared and compounded mixture of exosomes from bovine placenta was poured into the charging basket of a filling machine. Before starting the filling machine, the filling weight should be calibrated and recorded. During the filling process, a monitoring record of the filling process was required.

(2) Pre-freezing and vacuumizing: the product after filling was placed on the shelf of the lyophilizer, and the door of the lyophilizer was closed; after checking that the water pressure, current and air pressure met the conditions for starting the lyophilizer, the lyophilizer was started, the product was pre-frozen to below −40° C. in the front box, and the vacuum was controlled to 0.19 mbar;

(3) Primary sublimation: The product was pre-frozen to −40° C. and maintained for 190 min, and then the oil temperature for cooling was turned off and turned to the rear box for cooling. The condensing coil of the rear box was frozen to −50° C., and then the partition valve was opened, the vacuum pump and the vacuum control program were turned on to rise and maintain temperature in sequence. The moisture in the lyophilized powder was evaporated to the condensing coil for water capture and condensation.

(4) Secondary vacuum drying: after the primary drying was completed, the vacuum adjustment program of the lyophilizer was closed, and secondary vacuum drying was carried out. The residual moisture in the lyophilized powder was continued to be drained. The bottle temperature of the lyophilized powder should not exceed 32° C., and the process time should be kept for 6 h.

(5) Pressing the plug: After the secondary vacuum drying was completed, the hydraulic system of the lyophilizer was started to press the plug. After the plug is pressed, whether there is a jumping plug is observed. If there is no abnormality, release the vacuum in the lyophilizer.

TABLE 2

| Step | Set temperature (° C.) | Set time (min) | Duration (min) | |
|---|---|---|---|---|
| Pre-freezing | −40 | 1 | 190 | |

| | Set temperature (° C.) | | Duration (min) | |
|---|---|---|---|---|
| Freezing with condenser | −50 | | 1 | |

| | Pre-vacuumizing (mbar) | Alarm vacuum (mbar) | Alarm vacuum duration (s) | |
|---|---|---|---|---|
| Vacuumizing | 0.15 | 0.5 | 3000 | |

| | Set temperature (° C.) | Set time (min) | Duration (min) | Vacuum controlled (mbar) |
|---|---|---|---|---|
| Primary drying | −15 | 70 | 300 | 0.19 |
| | −10 | 60 | 300 | 0.19 |
| | −5 | 60 | 300 | 0.19 |
| | 0 | 60 | 220 | 0.19 |

| | Set temperature (° C.) | Set time (min) | Duration (min) | Vacuum controlled (mbar) |
|---|---|---|---|---|
| Secondary drying | 30 | 40 | 500 | 0.19 |
| | 30 | 1 | 120 | 0.0002 |
| Total time | | | 38 h | |

Example 7

The extract of exosomes from bovine placenta obtained by the method of Example 1 was thawed at room temperature and mixed with an excipient (2.0% mannitol, 1.0% trehalose, 1.0% glycine, 1.0% glycerol, 0.05% Tween, 0.5% albumin, and the balance is water) in a volume ratio of 1:1 to obtain a uniform mixture. The mixture was subjected to lyophilization in a sterile environment using a lyophilizer according to the procedure in Table 2 to obtain the lyophilized powder of exosomes from bovine placenta (Exo-02).

The extract of exosomes from bovine placenta obtained by the method of Example 1 was thawed at room temperature and mixed with an excipient (10.0% mannitol, 0.1% trehalose, 0.05% glycine, 5.0% glycerol, 0.01% Tween, 0.1% albumin, and the balance is water) in a volume ratio of 1:1 to obtain a uniform mixture. The mixture was subjected to lyophilization in a sterile environment using a lyophilizer according to the procedure in Table 2 to obtain the lyophilized powder of exosomes from bovine placenta (Exo-03).

The extract of exosomes from bovine placenta obtained by the method of Example 1 was thawed at room temperature and mixed with an excipient (5.0% mannitol, 0.4% trehalose, 0.06% glycine, 4.0% glycerol, 0.02% Tween, 0.2% albumin, and the balance is water) in a volume ratio of 1:1 to obtain a uniform mixture. The mixture was subjected to lyophilization in a sterile environment using a lyophilizer according to the procedure in Table 2 to obtain the lyophilized powder of exosomes from bovine placenta (Exo-04).

Example 8 Morphological Identification of Exosomes from Bovine Placenta

Figure 7:
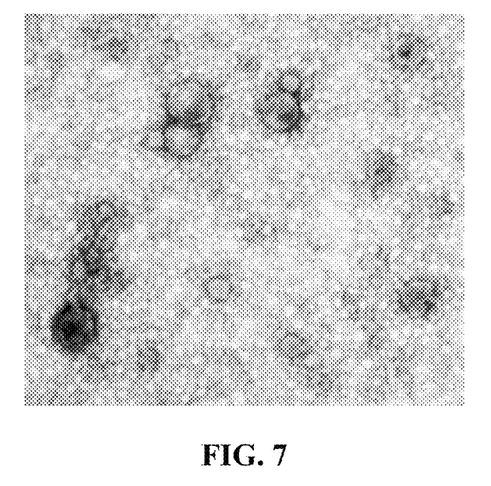
FIG. 7 shows the electron microscope picture of the exosomes from bovine placenta after reconstitution in Example 8.

The lyophilized powder of exosomes from bovine placenta prepared in Example 6 was resuspended in 500-1,000 µL of PBS. 10 µL was added dropwise to the copper grid of a transmission electron microscope for 1 min of precipitation, and the suspension was removed with filter paper. 10 µL of uranyl acetate was added dropwise to the copper grid of the transmission electron microscope for 1 min of precipitation, and the suspension was removed with filter paper. After drying at room temperature for several minutes, it was observed on the machine, and the results are shown in FIG. 7.

The results show that the exosomes reconstituted from the lyophilized powder of exosomes from bovine placenta had a diameter of about 100 nm and a round-cake structure with low refraction in the middle and high refraction around, which was a complete structure and conformed to the classical structure of exosomes.

Example 9 Exosomes Concentration and Nanoparticle Tracking Analysis (NTA) for Particle Size Detection The particle size and concentration of exosomes were analyzes by a nanoparticle tracking analyzer. The lyophilized powder of exosomes obtained in Examples 6 and 7 was dissolved in 1 mL of PBS which had been filtered through 0.22 µm, sealed and placed on ice. A disposable clean sample pool was used and wiped with a clean paper facing the light to ensure that no particles adhered to the outer tube wall on the light path. The exosome solution was slowly transferred to avoid air bubbles. The sample pool may be tilted moderately if required and was sealed with a lid. Then the sample pool was put into the instrument and detected according to the standard operating procedures. The data were saved and analyzed for the particle size range and concentration of exosomes, and the results are shown in Table 3, which show that the exosomes reconstituted from the lyophilized powder of the present disclosure had a relatively uniform particle size (30-150 nm) and a large number of particles.

TABLE 3

| Exosome sample | Average particle size (nm) | Concentration (Particles/mL) |
| --- | --- | --- |
| Exo-00 | 85.28 | 2.02E+10 |
| Exo-01 | 88.56 | 1.94E+10 |
| Exo-02 | 84.54 | 1.82E+10 |
| Exo-03 | 85.92 | 1.74E+10 |
| Exo-04 | 87.28 | 1.62E+10 |

Example 10 Western Blot Analysis of Exosomes

Figure 8:
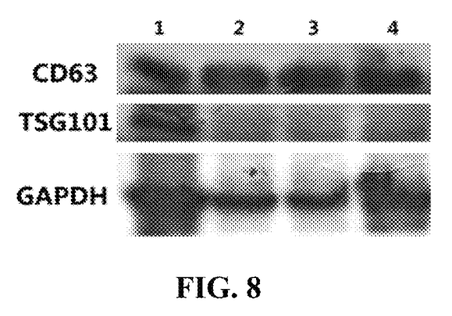
FIG. 8 shows the western blotting detection results of exosomes in Example 10.

The lyophilized powder prepared in Examples 6 and 7 was reconstituted, added with the protein lysis solution, placed on ice for 5-15 min and shaken 3-4 times during this period, each for 30 s. Then, centrifugation was carried out at 12,000 rpm for 5 min at 4° C., and the supernatant was transferred to a new centrifuge tube for Western blot in order to detect the expression of CD63 and TSG101 proteins. The results are shown in FIG. 8 that the exosomes reconstituted from the lyophilized powder prepared in Examples 6 and 7 of the present disclosure can detect the expression of CD63 and TSG101 proteins.

Example 11 Exosomes Promote Cell Proliferation

Figure 9:
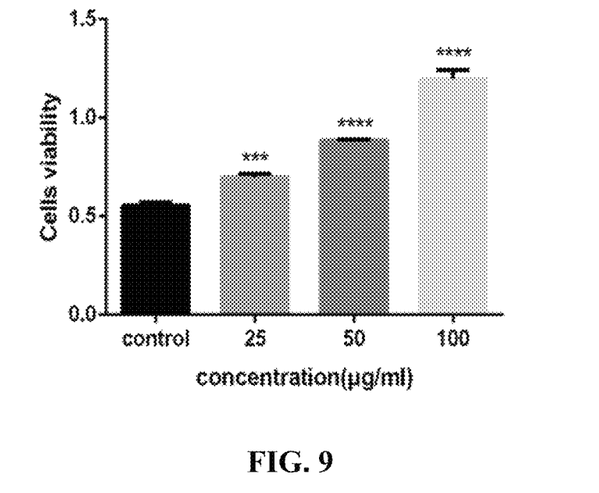
FIG. 9 shows the detection result of promoting cell proliferation activity by exosomes in Example 11.

The exosomes reconstituted from the lyophilized powder prepared in Example 6 was detected for activity by CCK8 method. The exosomes were added in the skin fibroblast medium according to the concentration gradient (0, 25, 50, 100 μg/ml) with a control without adding the lyophilized powder of exosomes. 48 hours later, CCK8 reagent was added to incubate for 2 h, and then the OD450 was detected by a microplate reader to calculate the cell viability. The results are shown in FIG. 9 that exosomes had a significant concentration-dependent effect on promoting cell proliferation.

Example 12 Comparison of Different Processes for Preparing Lyophilized Powder of Exosomes Lyophilized powder of exosomes was prepared from the placental exosomes and different excipients by different lyophilization processes. Control groups were set up for the experiment: the control without adding the lyophilized powder of exosomes and Comparative Examples 1-3, and the experimental groups: Examples 1 and 6.

Comparative Example A: exosomes from bovine placenta of Example 1 preserved in liquid (Exo-05);

Comparative Example B: the lyophilized powder prepared by the method of Example 1 in patent application No. 201910553008.3 "Exosome freeze-dried powder and preparation method and application thereof", labeled as Exo-06.

Comparative Example C: the lyophilized powder prepared by the method of Example 2 in the patent application No. 201410705636.6 "Method for preparing lyophilized powder of exosomes from human amniotic membrane mesenchymal stem cells", labeled as Exo-07.

Experimental group: lyophilized powder of Example 6 (Exo-01) and lyophilized powder of Example 7 (Exo-02).

Storage conditions: room temperature 25° C.

Comparative Examples A-C and the lyophilized powder of exosomes prepared in Examples 6 and 7 (Exo-01, Exo-02) were respectively placed at 25° C. for 6 months, reconstituted and subjected to exosome identification (nanoparticle size detection by NTA, Table 4).

TABLE 4

| Exosome sample | Average particle size (nm) | Concentration (Particles/mL) |
| --- | --- | --- |
| Exo-05 | 74.56 | 0.16E+10 |
| Exo-06 | 86.54 | 1.05E+10 |
| Exo-07 | 79.92 | 1.14E+10 |
| Exo-08 | 87.45 | 1.82E+10 |
| Exo-09 | 91.28 | 1.64E+10 |

Figure 10:
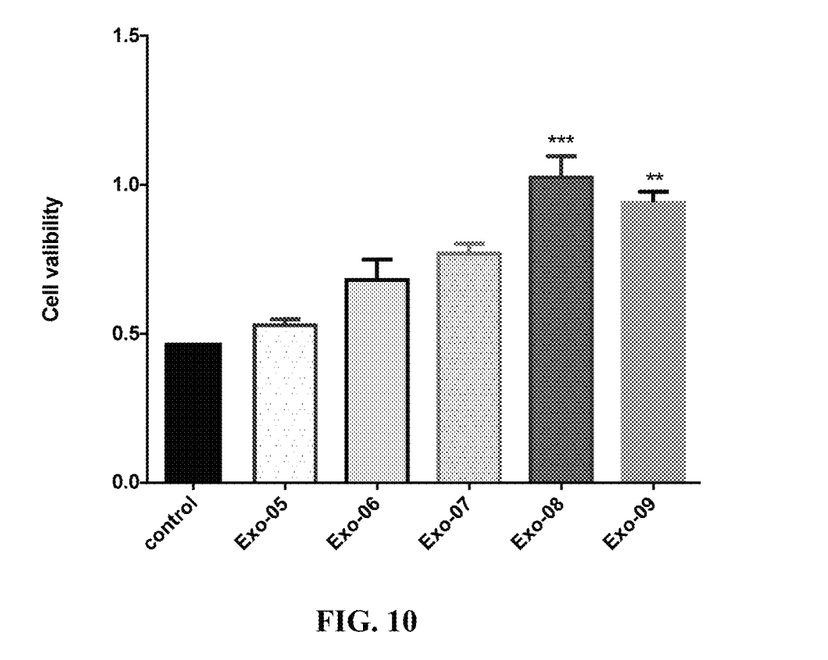
FIG. 10 shows the detection result of promoting cell proliferation activity by exosomes in Example 12.

Their biological activity was tested in a skin fibroblast proliferation model (CCK8 method) and results are shown in FIG. 10. Among them, the lyophilized powder of exosomes numbered Exo-01 and Exo-02 were re-numbered as Exo-08 and Exo-09 respectively after reconstitution. The results show that the lyophilized powder of Examples 6 and 7 of the present disclosure can maintain the integrity and biological activity of exosomes after reconstitution (Exo-08, Exo-09), and the result was significantly better than that of Comparative Examples A-C.

Comparative Example I

According to the component of each composition in Table 5, phase A was mixed, heated to 80±2° C., stirred until completely dissolved, and then cooled to 40±2° C.; and phase B was mixed well, added to phase A that had been cooled, and stirred uniformly to obtain composition 1.

Detected by an ultraviolet spectrophotometer, the transmittance of composition 1 was 79.13%.

TABLE 5

| Phase | Component | Mass % |
| --- | --- | --- |
| A | Water | The balance |
|  | Glycerol | 2 |
|  | Sodium hyaluronate | 0.2 |
|  | Hydroxylated lecithin | 1.5 |
| B | Polyglutamic acid | 0.8 |
|  | Tocopherol acetate | 0.05 |
|  | Total | 100 |

Example 13

According to the component of each composition in Table 6, phase A was mixed, heated to 80±2° C., stirred until completely dissolved, and then cooled to 40±2° C.; and phase B was mixed well, added to phase A that had been cooled, and stirred uniformly to obtain composition 2.

Detected by an ultraviolet spectrophotometer, the transmittance of composition 2 was 78.79%.

TABLE 6

| Phase | Component | Mass % |
| --- | --- | --- |
| A | Water | The balance |
|  | Glycerol | 2 |
|  | Sodium hyaluronate | 0.2 |
|  | Hydroxylated lecithin | 1.5 |

TABLE 6-continued

| Phase | Component | Mass % |
|---|---|---|
| B | Polyglutamic acid | 0.8 |
| | Tocopherol acetate | 0.05 |
| | Lyophilized powder of exosomes from bovine placenta | 0.5 |
| | Total | 100 |

Comparative Example II

According to the component of each composition in Table 7, phase A was mixed, heated to 80±2° C., stirred until completely dissolved, and then cooled to 40±2° C.; and phase B was mixed well, added to phase A that had been cooled, and stirred uniformly to obtain composition 3.

Detected by an ultraviolet spectrophotometer, the transmittance of composition 3 was 69.79%.

TABLE 7

| Phase | Component | Mass % |
|---|---|---|
| A | Water | The balance |
| | Glycerol | 17 |
| | Sodium hyaluronate | 0.02 |
| B | Glycine | 0.8 |
| | Tocopherol acetate | 0.15 |
| | Lyophilized powder of exosomes from bovine placenta | 0.5 |
| | Total | 100 |

Example 14

According to the component of each composition in Table 8, phase A was mixed, heated to 80±2° C., stirred until completely dissolved, and then cooled to 40±2° C.; and phase B was mixed well, added to phase A that had been cooled, and stirred uniformly to obtain composition 4.

Detected by an ultraviolet spectrophotometer, the transmittance of composition 4 was 85.16%.

TABLE 8

| Phase | Component | Mass % |
|---|---|---|
| A | Water | The balance |
| | Butanediol | 15 |
| | Trehalose | 2 |
| | Hydroxylated lecithin | 0.5 |
| B | Glycine | 0.8 |
| | Tocopherol acetate | 0.05 |
| | Lyophilized powder of exosomes from bovine placenta | 0.5 |
| | Total | 100 |

Example 15

According to the component of each composition in Table 9, phase A was mixed, heated to 80±2° C., stirred until completely dissolved, and then cooled to 40±2° C.; and phase B was mixed well, added to phase A that had been cooled, and stirred uniformly to obtain composition 5.

Detected by an ultraviolet spectrophotometer, the transmittance of composition 5 was 82.73%.

TABLE 9

| Phase | Component | Mass % |
|---|---|---|
| A | Water | The balance |
| | 1,3-Propanediol | 10 |
| | Sodium PCA | 1 |
| | Hydroxylated lecithin | 1 |
| B | Arginine | 0.8 |
| | Tocopherol acetate | 0.05 |
| | Lyophilized powder of exosomes from bovine placenta | 0.5 |
| | Total | 100 |

Example 16

According to the component of each composition in Table 10, phase A was mixed, heated to 80±2° C., stirred until completely dissolved, and then cooled to 40±2° C.; and phase B was mixed well, added to phase A that had been cooled, and stirred uniformly to obtain composition 6.

Detected by an ultraviolet spectrophotometer, the transmittance of composition 6 was 81.48%.

TABLE 10

| Phase | Component | Mass % |
|---|---|---|
| A | Water | The balance |
| | Glycerol | 10 |
| | Butanediol | 8 |
| | Hydroxylated lecithin | 1.5 |
| | Tocopherol acetate | 0.05 |
| B | Lyophilized powder of exosomes from bovine placenta | 0.5 |
| | Total | 100 |

Example 17

According to the component of each composition in Table 11, phase A was mixed, heated to 80±2° C., stirred until completely dissolved, and then cooled to 40±2° C.; and phase B was mixed well, added to phase A that had been cooled, and stirred uniformly to obtain composition 7.

Detected by an ultraviolet spectrophotometer, the transmittance of composition 7 was 80.99%.

TABLE 11

| Phase | Component | Mass % |
|---|---|---|
| A | Water | The balance |
| | Glycerol | 16 |
| | Trehalose | 2 |
| | Hydroxylated lecithin | 1.5 |
| B | Polyglutamic acid | 0.2 |
| | Tocopherol acetate | 0.05 |
| | Lyophilized powder of exosomes from bovine placenta | 0.5 |
| | Total | 100 |

Example 18

According to the component of each composition in Table 12, phase A was mixed, heated to 80±2° C., stirred until completely dissolved, and then cooled to 40±2° C.; and phase B was mixed well, added to phase A that had been cooled, and stirred uniformly to obtain composition 8.

Detected by an ultraviolet spectrophotometer, the transmittance of composition 8 was 96.48%.

TABLE 12

| Phase | Component | Mass % |
| --- | --- | --- |
| A | Water | The balance |
|   | Butanediol | 10 |
|   | Sodium hyaluronate | 0.2 |
|   | Hydroxypropyl cyclodextrin | 4.8 |
| B | Arginine | 0.8 |
|   | Tocopherol glucoside | 2 |
|   | Lyophilized powder of exosomes from ovine placenta | 0.5 |
|   | Total | 100 |

Example 19

According to the component of each composition in Table 13, phase A was mixed, heated to 80±2° C., stirred until completely dissolved, and then cooled to 40±2° C.; and phase B was mixed well, added to phase A that had been cooled, and stirred uniformly to obtain composition 9.

Detected by an ultraviolet spectrophotometer, the transmittance of composition 9 was 63.81%.

TABLE 13

| Phase | Component | Mass % |
| --- | --- | --- |
| A | Water | The balance |
|   | Tremella polysaccharide | 18 |
|   | Soybean lecithin | 0.05 |
| B | Proline | 1 |
|   | Tocopherol polyether | 0.02 |
|   | Lyophilized powder of exosomes from porcine placenta | 1.5 |
|   | Total | 100 |

Example 20

According to the component of each composition in Table 14, phase A was mixed, heated to 80±2° C., stirred until completely dissolved, and then cooled to 40±2° C.; and phase B was mixed well, added to phase A that had been cooled, and stirred uniformly to obtain composition 10.

Detected by an ultraviolet spectrophotometer, the transmittance of composition 10 was 92.85%.

TABLE 14

| Phase | Component | Mass % |
| --- | --- | --- |
| A | Water | The balance |
|   | Sodium PCA | 1 |
|   | Cyclodextrin | 0.05 |
| B | Methionine | 2.5 |
|   | Tocopherol phosphate | 1.5 |
|   | Lyophilized powder of exosomes from horse placenta | 1 |
|   | Total | 100 |

Example 21

According to the component of each composition in Table 15, phase A was mixed, heated to 80±2° C., stirred until completely dissolved, and then cooled to 40±2° C.; and phase B was mixed well, added to phase A that had been cooled, and stirred uniformly to obtain composition 11.

Detected by an ultraviolet spectrophotometer, the transmittance of composition 11 was 74.83%.

TABLE 15

| Phase | Component | Mass % |
| --- | --- | --- |
| A | Water | The balance |
|   | Glycerol | 20 |
|   | Hydroxylated lecithin | 4 |
| B | Valine | 4.5 |
|   | Tocopherol acetate | 0.1 |
|   | Lyophilized powder of exosomes from horse placenta | 4.5 |
|   | Total | 100 |

Example 22

This example of the present disclosure provides the detection of the number of exosome vesicles in compositions 1-11, and the steps are as follows:

After the compositions 1-11 prepared above were sealed and stored in the dark for 15 days at room temperature, they were observed for morphology under a transmission electron microscope at 5000× magnification, and the intact vesicles were counted. The mean value of the number of intact vesicles observed in three observations was summarized and shown in Table 16.

TABLE 16

| Sample | Number of intact vesicles |
| --- | --- |
| Composition 1 | 0 |
| Composition 2 | 18.33 |
| Composition 3 | 6 |
| Composition 4 | 12.67 |
| Composition 5 | 15.67 |
| Composition 6 | 8.67 |
| Composition 7 | 16.33 |
| Composition 8 | 19.67 |
| Composition 9 | 9 |
| Composition 10 | 10.33 |
| Composition 11 | 21.67 |

As can be seen from Table 16, the number of intact vesicles in composition 1 (containing no exosomes from bovine placenta) was 0; as for compositions 2-5, the order of the number of intact vesicles was composition 2>composition 5>composition 4>composition 3, which corresponded to the content of hydroxylated lecithin in the composition (composition 2>composition 5>composition 4>composition 3), indicating that hydroxylated lecithin had a protective effect on the vesicle structure of exosomes from bovine placenta. As for compositions 2, 6 and 7, the order of the number of intact vesicles was composition 2>composition 7>composition 6, which corresponded to the content of amino acids in the composition (composition 2>composition 7>composition 6), indicating that amino acids have a protective effect on the vesicle structure of exosomes from bovine placenta.

Example 23

This example of the present disclosure provides the essence product prepared from composition 1, and the specific preparation method is as follows:

According to the component of each composition in Table 17, phase A was mixed, heated to 85±2° C., stirred until completely dissolved, maintained at this temperature for 30 min, and then cooled to 40±2° C.; and phase B was added to phase A that had been cooled, stirred uniformly and then cooled to room temperature to obtain Essence I.

TABLE 17

| Phase | No. | Raw material | Weight ratio (%) |
|---|---|---|---|
| A | 1 | Water | The balance |
|   | 2 | Glycerol | 5 |
|   | 3 | Butanediol | 4 |
|   | 4 | Disodium EDTA | 0.05 |
|   | 5 | Ammonium acryloyldimethyltaurate/VP copolymer | 0.3 |
|   | 6 | Methylparaben | 0.2 |
|   | 7 | Allantoin | 0.2 |
| B | 8 | Composition 1 | 20 |
|   | 9 | Leaf extract of Aloe Barbadensis | 1 |
|   | 10 | Phenoxyethanol | 0.4 |
|   | 11 | Ethylhexylglycerol | 0.3 |

Example 24

This example of the present disclosure provides the essence product prepared from composition 2. The specific preparation method is with reference to Example 23, and the difference is that in the present example, the No. 8 raw material in phase B was replaced by composition 2, and the remaining steps are the same as Example 23. Essence II was obtained.

Example 25

This example of the present disclosure provides the essence product prepared from composition 3. The specific preparation method is with reference to Example 23, and the difference is that in the present example, the No. 8 raw material in phase B was replaced by composition 3, and the remaining steps are the same as Example 23. Essence III was obtained.

Example 26

This example of the present disclosure provides the essence product prepared from composition 4. The specific preparation method is with reference to Example 23, and the difference is that in the present example, the No. 8 raw material in phase B was replaced by composition 4, and the remaining steps are the same as Example 23. Essence IV was obtained.

Example 27

This example of the present disclosure provides the anti-skin aging observation test of the above four essences, and the specific steps are as follows:

1. Essences I, II, III and IV prepared in the above examples were served as cosmetic to be tested.

2. 80 female volunteers with wrinkled skin, aged 29-45 years old, with an average age of 34 years old, were under test, and they were all indoor clerks in the same office building. The volunteers did not use other anti-wrinkle products during the test period. The area within the lines connected by three points, the inner corner of the eyes, corners of the mouth and the temple, was selected as the test area.

3. The skin wrinkle and smoothness of the volunteers' face test area before applying cosmetics were measured with a Visia skin tester.

4. The volunteers were randomly divided into 4 groups with 20 in each group. The essences of Examples 23-26 were used in the test area respectively, and each essence was used in an amount of about 0.8 g each night from 20:00 to 22:00, and stayed for at least 8 hours.

5. After 10, 20 and 30 days of continuous use of cosmetic products, the skin texture was tested with a Visia skin tester.

6. The numerical value measured in the test area of the subject each time was recorded, and day 0 was used as a benchmark to compare and analyze skin wrinkles and smoothness, and evaluate the improvement of the essence on the skin texture. After using Essences I, II, III and IV respectively for 30 days, the statistics results are shown in Table 18.

TABLE 18

| Sample | Wrinkle improvement rate (%) | | | Smoothness improvement rate (%) | | |
|---|---|---|---|---|---|---|
|  | Day 10 | Day 20 | Day 30 | Day 10 | Day 20 | Day 30 |
| Essence I | 5.3 | 7.1 | 8.6 | 5.3 | 7.7 | 8.3 |
| Essence II | 7.7 | 20.2 | 25.6 | 7.6 | 19.9 | 25.3 |
| Essence III | 6.2 | 13.8 | 15.3 | 5.7 | 13.2 | 14.6 |
| Essence IV | 6.8 | 15.6 | 19.5 | 6.6 | 15.3 | 20.0 |

As can be seen from the test results in Table 18, the wrinkle improvement rate and smoothness improvement rate of Essence II and Essence III on skin were better than that of Essence I, indicating that the composition containing exosomes from bovine placenta of the present disclosure had obvious anti-wrinkle effect. The wrinkle improvement rate and smoothness improvement rate of Essence II were better than that of Essence III, indicating that hydroxylated lecithin can improve the anti-wrinkle effect of the system. The wrinkle improvement rate and smoothness improvement rate of Essence II, Essence III and Essence IV on skin were in the order of Essence II>Essence IV>Essence III, among which Essence II had more hydroxylated lecithin than Essence IV and Essence III did not contain hydroxylated lecithin, indicating that hydroxylated lecithin can improve the anti-wrinkle effect of the system.

To sum up, the compositions provided by the examples of the present disclosure had excellent light transmittance that was not lower than 60% of the transmittance of pure water under the same test conditions, and can be directly used in skin care products of transparent systems without turbidity. Compared with composition 1, compositions 2-11 contained exosome vesicles structure; compared with composition 3, composition 2 and compositions 4-11 had intact exosome vesicle structure, and the retention rate of exosome vesicles was significantly improved; compared with Essence I, Essence II, Essence III and Essence IV had a dramatic effect on wrinkle improvement and smoothing.

The above is only the preferred embodiment of the present disclosure, it should be pointed out that for those of ordinary skill in the art, several improvements and modifications can be made without departing from the principle of the present disclosure, and these improvements and modifications should also be considered within the scope of protection of the present disclosure.

The invention claimed is:

1. A method for preparing exosomes from bovine placenta comprising:
   homogenizing bovine placenta to obtain a homogenate, and subjecting the homogenate to freeze-thaw process, wherein the freeze-thaw process comprises freezing at −80° C. for 24 h and then thawing at room temperature, and the freeze-thaw process is performed once;
   performing a first round of ultrasonic treatment on the thawed homogenate and filtering, and freezing the filtrate at −80° C., wherein power of the first round of ultrasonic treatment is 990 w and time is 30 min;
   thawing the filtrate at 4° C. and centrifuging to obtain a supernatant, performing a second round of ultrasonic treatment on the supernatant, and performing multiple filtrations through filters to obtain the exosomes from bovine placenta;
   wherein the second round of ultrasonic treatment is performed once at an interval of 8 s, each ultrasonic treatment lasts for 8 s, the power of the second round of ultrasonic treatment is 500 w, and the total time of ultrasonic treatment is 30 min; and
   the multiple filtrations are four filtrations, through filter meshes with pore sizes of 5 μm, 1 μm, 0.45 μm and 0.22 μm in sequence.

* * * * *